US00PP21834P2

(12) United States Plant Patent
Felker et al.

(10) Patent No.: US PP21,834 P2
(45) Date of Patent: Apr. 5, 2011

(54) CACTUS PEAR PLANT NAMED 'DAR 1-21-27 PURPLE'

(50) Latin Name: ***Opuntia ficus-indica* L. Miller**
Varietal Denomination: DAR 1-21-27 Purple

(75) Inventors: Peter Felker, Salinas, CA (US); Ronald A Bunch, Salinas, CA (US)

(73) Assignee: D'Arrigo Bros. Co., of California, Salinas, CA (US)

( * ) Notice: Subject to any disclaimer, the term of this patent is extended or adjusted under 35 U.S.C. 154(b) by 0 days.

(21) Appl. No.: 12/584,816

(22) Filed: Sep. 14, 2009

(51) Int. Cl.
*A01H 5/00* (2006.01)

(52) U.S. Cl. ..... Plt./156

(58) Field of Classification Search ..... Plt./156, Plt./372
See application file for complete search history.

(56) References Cited

OTHER PUBLICATIONS

Mondragon-Jacobo et al. "Native Cultivars of Cactus Pear in Mexico," 1996, p. 446-450. In: J. Janick (ed). Progress in new crops. ASHS Press, Arlington, VA.*
Barbera et al.,1992 Physical, morphological and chemical changes during fruit development and ripening in three cultivars of prickly pear. J Hort Sci 67:307-312.
Felker et al., 2005.Comparison of *Opuntia ficus indica* varieties of Mexican and Argentine origin for fruit yield and quality in Argentina. J. Arid Env 60:405-422.
Stintzing et al.,2005.Color, Betalain Pattern and Antioxidant Properties of Cactus pear (*Opuntia* sp.). J. Agric Food Chem 53:442-451.
Mondragon and Gonzalez. 1994. Reyna (syn. Alfajayucan) is the leading cactus pear cultivar in Central Mexico. Fruit varieties journal. 48: 134-136.
Mondragon and Gonzalez. 1996. Native cultivars of cactus pears in Mexico. p. 446-450 In: J.Janick (ed), Progress in new crops. ASHS Press, Arlington, VA.
Mondragon. 2001.Verification of the Apomictic Origin of Cactus Pear (*Opuntia* spp) seedlings of OP and Crosses from Central Mexico. J. Prof Assn Cactus Dev 4: 49-56.
Nerd et al., 1991. Out of season prickly pear: fruit characteristics and effect of fertilization and short droughts on productivity. HortScience 26: 337-342.
Parish and Felker 1997.Fruit quality and production of cactus pear (*Opuntia* spp) clones selected for increased frost hardiness. Journal of Arid E.nvironments 37: 123-143.
UPOV, 2006. Cactus pear and xoconostles. TG/217/2. International Union for the protection of new varieties of plants. Geneva.
Wang et al., 1996. Cross-hybridization and seed germination in *Opuntia* species. J. Prof Assn Cactus Dev 1:49-60.

* cited by examiner

*Primary Examiner* — Susan B McCormick Ewoldt

(57) ABSTRACT

A new and distinct variety of cactus pear having the following unique combination of desirable features:
1. A fruit with a purple colored edible interior portion.
2. An average Brix of 14.9%
3. An average firmness of the pulp of 3.0 lb
4. An average pulp percentage of 48%.
5. A fruit weight ranging from 130 to 200 g.

5 Drawing Sheets

Latin name of the genus and species of the plant claimed: *Opuntia ficus-indica* L. Miller.

Variety denomination: 'DAR 1-21-27 Purple'.

No federal or state sponsored research funding was used in the development of these materials.

BACKGROUND OF THE INVENTION

Fruits of spiny and spineless *Opuntia ficus indica* are about 110-180 grams, range from 12 to 15% total soluble solids (Brix), have a variety of fruit colors, i.e. green, orange, red and purple, and have been grown in many arid regions of the world such as Mexico, Brazil, Chile, Argentina, Spain, Italy, Israel, and South Africa for commercial fruit production (Parish and Felker, 1997). The market use of the fruit is to be consumed fresh after the peel is removed. Mexico is the world center of production with great variation in spines, fruit colors, dates of maturity and Brix (Mondragon and Gonzalez, 1996). While the lime green variety 'Reyna' is the leading cactus pear variety in Mexico (Mondragon and Gonzalez, 1994), this variety has long spines that prevent its cultivation in the USA due to objections from harvesting crews. Mondragon and Gonzalez, (1996) have reported fruits of many colors, but they have not provided experimental details on field design, laboratory methods or coefficients of variation for these properties and they do not provide data on firmness of the edible inner portion which Felker et al., (2005) have suggested needs to be greater than 2.2 lb for a good quality fruit. Moreover D'Arrigo Bros data on fruit Brix, firmness, weight, peel thickness, percentage of edible portion on more than 30,000 fruit of existing varieties and progeny of new crosses is not in agreement with Brix values of 15-16 for red or purple colored fruits reported by Mondragon and Gonzalez, (1996). *Opuntia* fruit data, from refereed journal articles with field and laboratory experimental details and estimates of variation, have been provided by Barbera et al., (1992), Nerd et al., (1991) and Felker et al., (2005).

In 1998, copies of the more than 100 *Opuntia* clones obtained from Kingsville, Tex. (that were later deposited in the USDA *Opuntia* germplasm collection in Parlier, Calif.) that represented all of the major types present in Mexico, South Africa, Argentina and Chile. As described below, none of the existing cultivars met the objectives of high pulp firmness (>2.8 lb), high Brix, (>14), thornlessness and purple color in the same plant and therefore hybridizations were conducted to obtain the desired variety. This collection included the Kingsville, Tex. accession 1279 with dark purple flesh, and is similar to the 'Charola' described by Mondragon and Gonzalez (1996).

There are extensive plantations of cactus pear for fruit in the Mediterranean, principally Sicily, but also Spain and Israel. *Opuntia ficus indica* was brought to Spain on one of the first voyages of Christopher Columbus from where it spread to the rest of the Mediterranean region. In the largest commercial production area of the Mediterranean in Sicily, there are 3 varieties, 'Rossa' (with red fruit), 'Gialla' (with yellow fruit) and 'Bianca' (with almost colorless fruit) (Barbera et al., 1992). These three varieties were essentially the same with regard to fruit quality with a maximum Brix of about 13% (Barbera et al., 1992). Nerd et al., (1991) in Israel, found the Brix of the summer 'Ofer' variety (which is yellow and similar to the 'Gialla' from Sicily) to be 11.8% in the winter and 12.8% in the summer. In Argentinean field trials, Texas A&M Kingsville (TAMUK) accession 1281 (which is very similar to the Italian 'Rossa') and TAMUK 1277 and 1320 (which are similar to Italian 'Gialla') had Brix values of about 12.6, 12.7 and 13.0 respectively (Felker et al., 2005).

In spite of acceptable fruit sugar concentrations of about 13% in high yielding varieties, such as Italian 'Rossa' and 'Gialla' types (including 1281, 1277, 1320), these varieties have very low pulp firmness of about 2 lb (versus 4 lb for spiny orange 1287 and green fruited Argentine and Chilean varieties) which lead to poor consumer acceptance in Argentina (Felker et al., 2005). While firmness is the parameter measured, the objectionable quality is that pulps with low firmness value lack structural integrity and may break apart when the peel is separated from the pulp. A pulp firmness of about 2.2 lb has been suggested as the minimum acceptable for cactus fruit (Felker et al., 2005).

In the USA, the only commercial variety, the 'Andyboy Red', is similar to the Italian 'Rossa' and has a Brix of about 13.5 in the summer crop but maybe as low as 10.5 in the mid winter crop. Perhaps due to the cooler weather of the growing region in the USA, the red fruits do not break apart when peeled, but they are not as firm and juicy as other types. The 'Andyboy Red' is also in the low range of pulp firmness of about 2 lb. In the USA, the major demand from consumers is for the red colored fruit, which also has higher antioxidant values than the yellow or green fruits, but is less than the purple ones (Stintzing et al., 2005).

In addition to the published work on the lack of firmness and Brix in red and purple colored fruits, one of us (PF) has visited cactus plantations in South Africa, Italy, Mexico, Chile and Argentina and has not found firm, high Brix purple fruits in any existing germplasm collection.

Due to the attractive dark purple color and the higher antioxidant values of the purple fruit than red, orange and green ones (Stintzing et al., 2005), it would be very useful to have a purple fruit with high Brix and firmness. In Argentine field trials (Felker et al., 2005), the pulp firmness of two purple varieties TX 1279 and TX 1300 were approximately 2 lb and thus below what we believe is a commercial desirable. Also these two varieties had Brix values of 13.0 and 11.9 respectively. There is purple fruit variety of *Opuntia ficus- indica* in Mexico named 'V1' but it is not in commercial production in Mexico, probably as it does not have as high a Brix or is as firm as the green 'Reyna.' Occasionally in Mexico, fruits of *Opuntia robusta,* known as 'Tapona' are consumed since they are the first fruits to mature. Data on these fruits show that while they have a moderate Brix, they are much softer than all other commercial varieties and thus not appreciated.

Therefore using the basic crossing technique of Wang et al., (1996), hybrids were made between high firmness, high Brix fruits of other varieties and commercial high producing, low Brix, low firmness purple fruited varieties to develop a high Brix, high firmness purple fruit with a good commercial yield. Progeny of various crosses were planted near Chualar, Calif. and evaluated for Brix and firmness using previously described techniques (Felker et al., 2005). About one dozen clones of each color class (green, orange, red and purple) from more than 3000 progeny of various crosses were selected and planted in a randomized complete block trial with four replicates (with one plant per replicate) to directly compare fruit characters for these advanced selections. For two years, several fruits were taken from each of the four replicates, once a month from about September till May. The best purple fruited variety of this randomized complete block trial, originally from Block 1, row 21 plant 27 of this trial was found to have the best overall combination of characters and is the subject of this patent. The parents of this plant were a spineless purple fruited accession R7-54:1-01-22 and a spineless green fruited plant R7:53YT:1-01-05 from our germplasm collection. None of the parents have been patented or have patent pending.

Asexual propagation

All cactus pear varieties are asexually propagated by cutting an approximate one year old cladode from the mother plant, allowing the cut scar to heal over for approximately 2 weeks and then planting this unrooted cladode (botanically a portion of a dicot stem) about ⅓ of its height into dry soil. If the cladodes do not rot, 100% of them will root in less than a month without any hormone treatments.

Apomixis, that is the asexual reproductive process that occurs in the ovule of flowering plants, frequently occurs in *Opuntia ficus indica* (Mondragon-Jacobo, 2001). While the ratio of apomictic seedlings to seedlings resulting from fertilization varies greatly among female parents, we have found that apomixis occurs in this new variety. Thus this variety could be propagated asexually from apomictic seedlings. It is envisioned that this variety could be genetically engineered to include other traits.

This variety is asexually propagated by planting unrooted cladodes. The claimed plant retains its distinctive characteristics and reproduces true to type in successive generations.

BRIEF SUMMARY OF THE INVENTION

This invention relates to overcoming soft, low Brix characteristics in purple fruited cactus pears by controlled hybridization to produce cactus pears with significantly greater fruit firmness and total soluble solids (Brix).

DETAILED BOTANICAL DESCRIPTION

Figure 1:
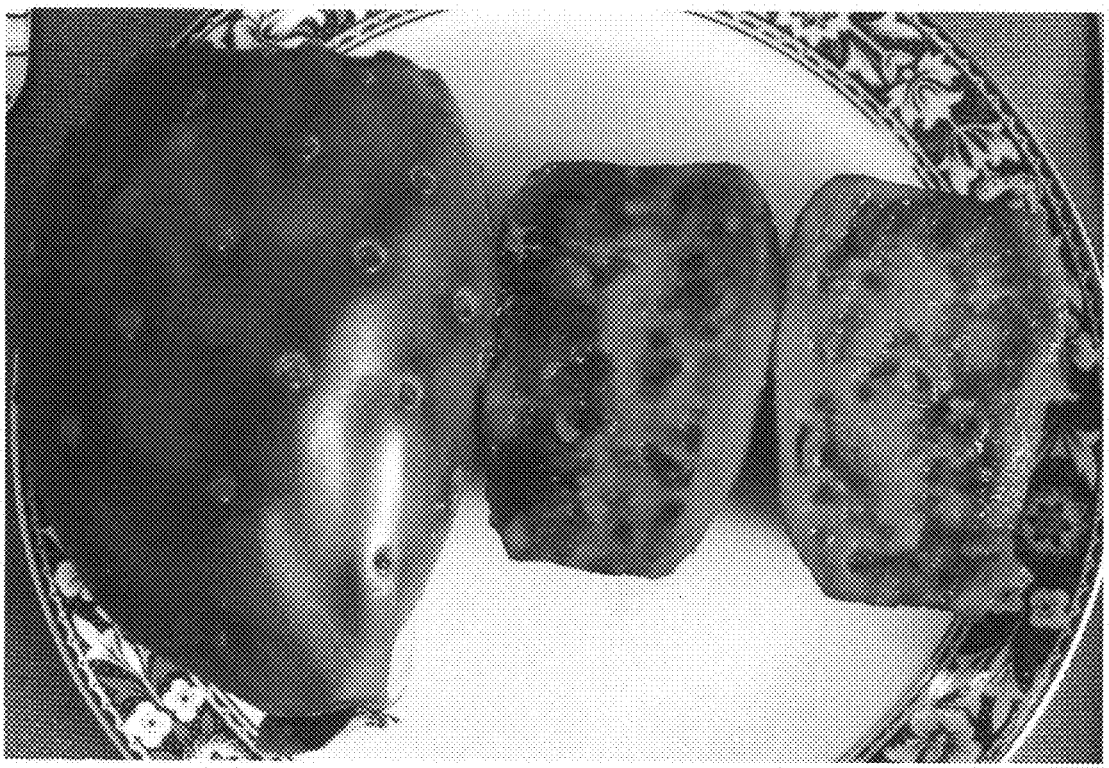
In FIG. 1 can be seen the exterior and interior view of fruits of 'DAR 1-21-27 Purple' at optimal harvest conditions after the spines and glochids have been removed.
Figure 2:
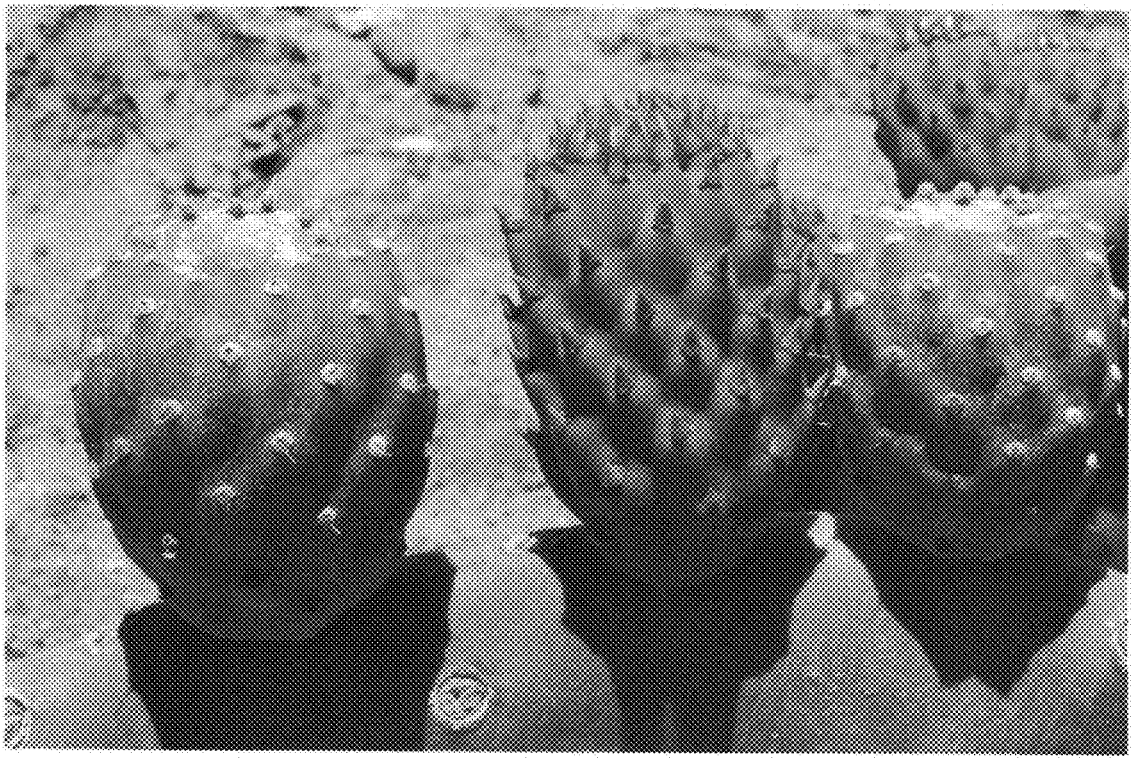
In FIG. 2 can be seen immature fruits of 'DAR 1-21-27 Purple' showing the lack of glochids.

The color chart used in this specification follows The Royal Horticultural Society Color Chart year 1996. The fruits have an oblong shape. At optimal harvest conditions, the external peel color is about 59A, while the interior edible portion of the fruit ranges from 60A that is the purple matrix, to 65B that is the whitish interior. This 65B whitish center is probably the most single important distinguishing character from other purple fruited varieties. Other red and purple varieties are too soft if harvested when 100% of the fruit surface has the red or pink color and must be harvested when only 50-60% of the fruit is covered with this reddish/purple color. In contrast, due to the high firmness, this variety can be harvested when the external peel color is 100% purple. There are about 51 areoles per fruit in which the number of glochids per areola greater than 2 mm in length is 0. Unlike other varieties that have glochids greater than 2 mm in length in the cool weather in the area where these fruits are grown, there are no glochids longer than 1 mm on the immature fruits as can be seen in FIG. 2. However there are fewer than 100 glochids per areole less than 1 mm in length. There is no pubescence. According to the UPOV classification, the stalk length is short and the classification of the floral scar depression is 3. The peel thickness is about 10 mm.

Figure 3:
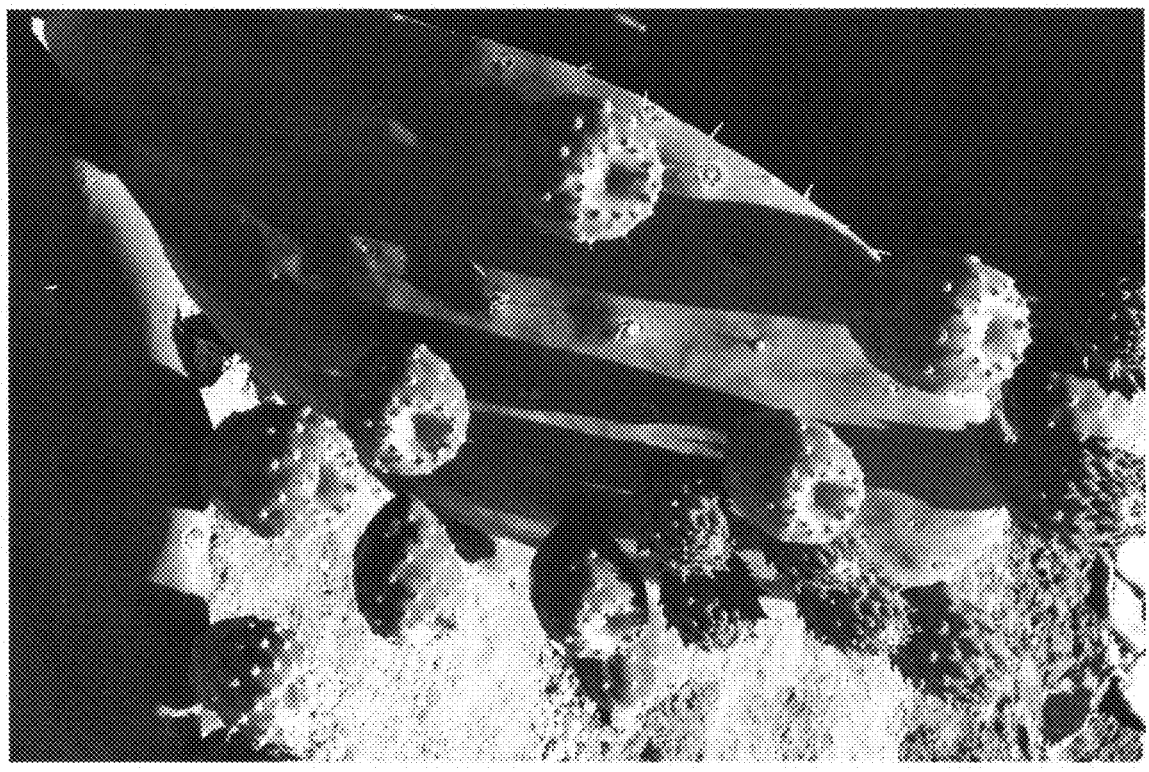
FIG. 3 illustrates a one year old cladode of 'DAR 1-21-27 Purple' showing spines on the flat surface and margins of a cladode.
Figure 4:
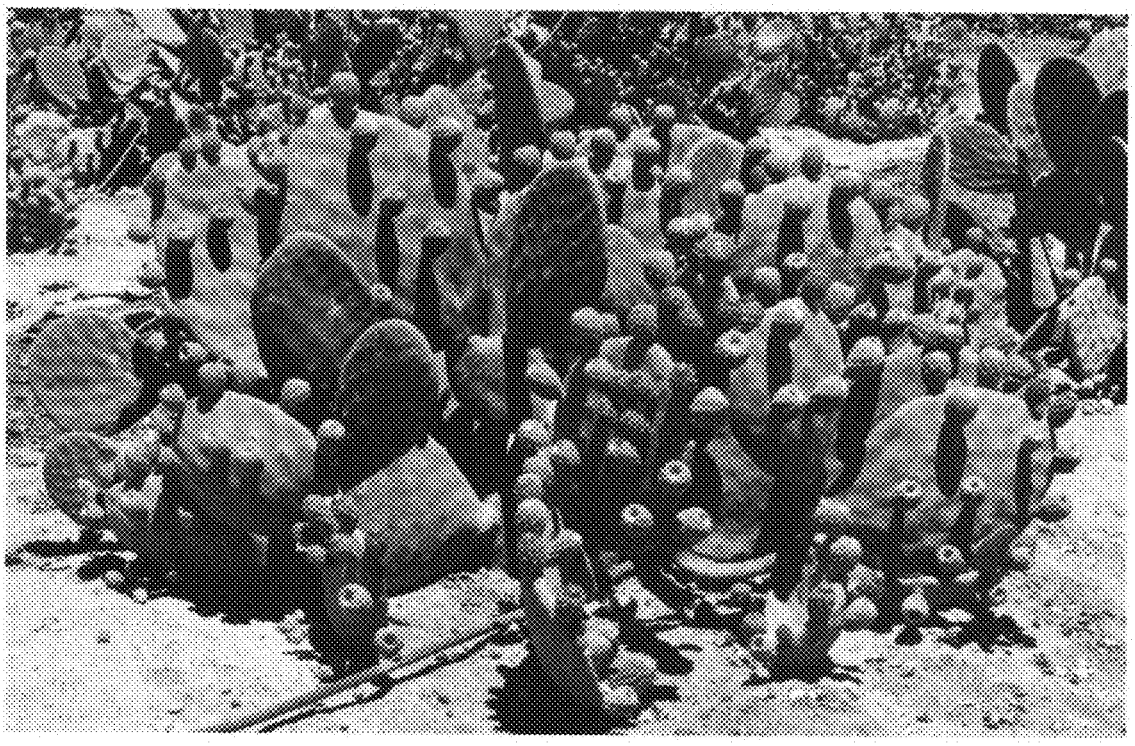
FIG. 4 shows a mature compact plant of 'DAR 1-21-27 Purple' that was thinned to increase fruit size.
Figure 5:
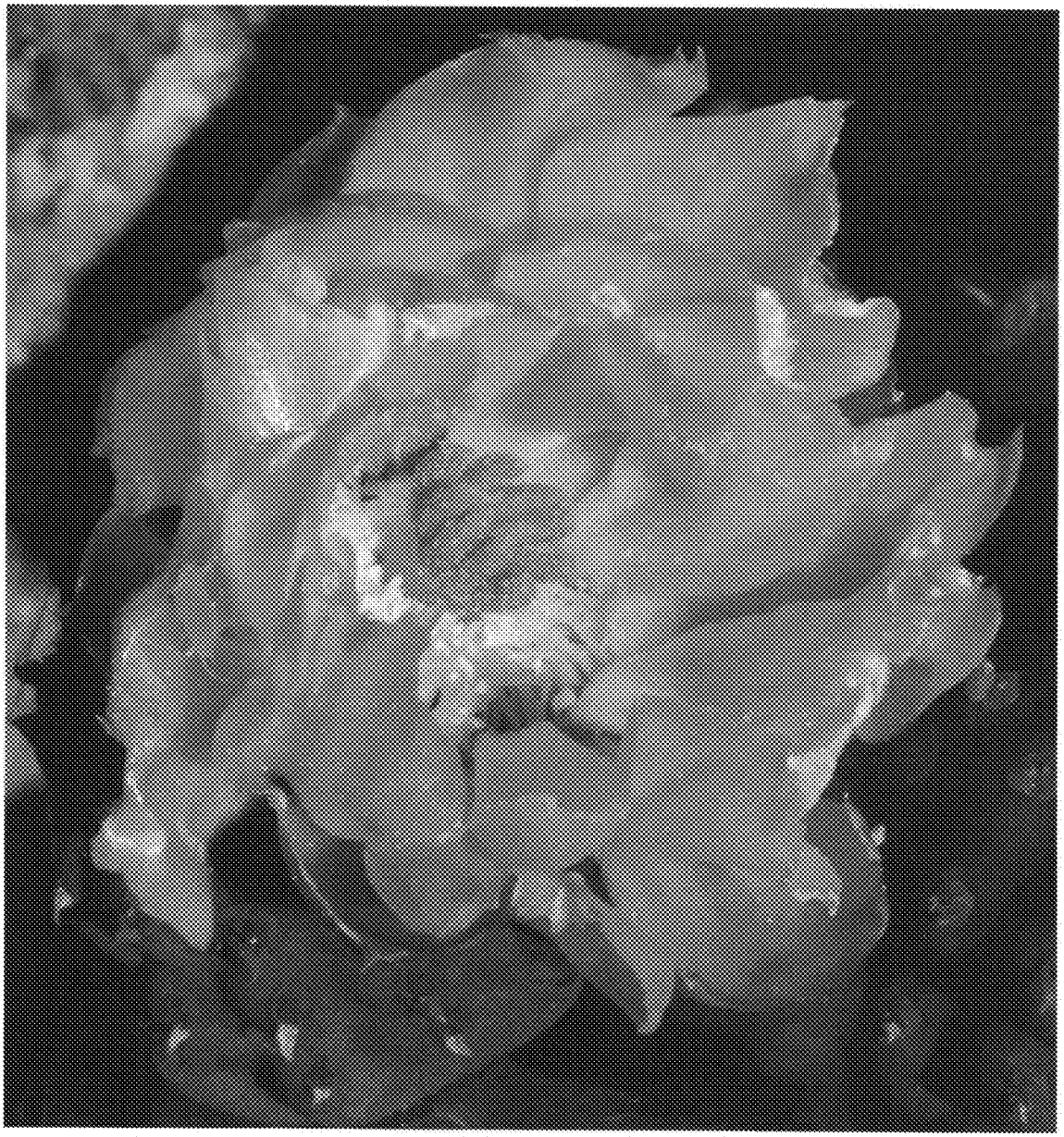
FIG. 5 shows an open flower of 'DAR 1-21-27 Purple' showing petal colors, stigma and dehiscing anthers.

While this variety does not have multiple, long (3-5 cm) spines coming out from each areole of the cladodes as do *Opuntias* from the wild, it does have single small semi erect spines of color 155D about 10 mm in length coming out of some of the areoles FIG. 3. These spines occur most frequently on the margins of the cladode but can also be seen on the flat side of the cladodes. There are about 42 areoles per cladode with a color of 166A. There are no glochids on one year old mature pads. The cladodes, which have a color of 137C, have a smooth surface that is not waxy or pubescent. The sizes of the cladodes are greatly influenced by the climate and growing conditions. Nevertheless, near Gonzalez, Calif. where these plants are grown, a typical mature pad would have a broad obovate shape and be about 40 cm long, 32 cm wide and 2.1 cm thick. Most of the cladodes are flat without a concave aspect. A mature 4 year old plant is about 4 meters wide and 2.5 meter tall.

The flower diameter is about 6 cm and the length of the flower only (not including the immature supporting bud) is about 3 cm long. The length of supporting immature bud, when the flower is open, varies from about 2 cm to 5 cm depending on season of the year and moisture/fertility conditions. The flowers lack fragrance. The color of the broad elliptic shaped petals ranges from about a 23A yellow-orange group on the inside of the petals to 60A on the outside of the petals. Only one stigma, with a height of about 7 mm, occurs with a light green color (144B). The style has a color of 57D. There are about 500 stamens per flower that are about 10 mm long and that have color 2D. Anthesis, in the location where the plants are grown, peaks in May and June depending on the weather but some anthesis occurs as late as November. The flowers are not pollinated by honey bees but rather by a specialized cactus bee that makes its nest in holes in the ground.

In Table 1 can be found a comparison of the means and 95% confidence intervals for 93 analyses of Texas A&M 1281 which is a red fruited variety, that is very similar to the commercial 'Rossa' from Italy, and our new variety 'DAR 1-21-27 Purple'. It is to be noted that the Brix of 12.7, fruit size of 145 grams and 55% pulp percentage are similar to published values for the 'Rossa' variety described above. In contrast the average of 154 analyses for 'DAR1-21-27' purple shows a 2% increase in Brix (from 12.7 to 14.9), a 58% increase in firmness (from 1.9 to 3.0) but a slight decrease in pulp percentage (from 55 to 48). The average fruit weight of 'DAR1-21-27' is smaller than 1281, but we believe the much greater eating quality will make up for this difference. The fruit size of 'DAR1-21-27' is very susceptible to cultural management and we have been able to increase this size with cultural practices. Additionally when compared to two accessions of purple fruit from Mexico (TX 1279 and V1), one of which (V1) is one of the most important purple cultivars, both the Brix and firmness of the new 'DAR 1-21-27 Purple' is statistically greater at the 95% probability level than either TX 1279 or V1. Table 1 A comparison of new 'DAR 1-21-27 Purple' *Opuntia ficus indica* with purple fruit to a standard commercial red type fruit TX 1281 and two varieties with purple fruit from Mexico (TX 1279 and V1).

| Variety | Number of analyses | Average of Brix (%) | 95% CI of Brix | Average of firmness (lb) |
|---|---|---|---|---|
| 'DAR 1-21-27 Purple' | 154 | 14.9 | 0.22 | 3.0 |
| TX1281 | 93 | 12.7 | 0.22 | 1.9 |
| TX1279 | 101 | 13.5 | 0.15 | 2.1 |
| V1 Mexico | 83 | 13.1 | 0.22 | 2.1 |

| Variety | 95% CI of firmness | Average of Fruit weight (g) | 95% CI of fruit weight | Average of pulp percent (%) | 95% CI of pulp percent |
|---|---|---|---|---|---|
| 'DAR 1-21-27 Purple' | 0.15 | 136.7 | 7.0 | 48 | 1.4 |
| TX1281 | 0.08 | 145.5 | 5.4 | 55 | 1.3 |
| TX1279 | 0.09 | 164.2 | 8.1 | 45 | 1.3 |
| V1 Mexico | 0.1 | 147.7 | 8.2 | 45 | 1.7 |

With regard to seed content, the TX 1281 had 4.59 grams of seeds per 100 gram of edible pulp (with a 95% confidence interval of 0.56) while the 'DAR1-21-27 Purple' had 5.16 grams of seeds per 100 grams of pulp (with a 95% confidence interval of 1.33).

In the area where these cacti are grown commercially in Gonzalez, Calif., approximately 40 km from the Pacific Ocean, the maximum daily temperatures during the growing season rarely exceed temperatures of 30 C for more than a few hours. However occasionally in the fall of the year, the orchards experience daily maximum temperatures of 35 C for several days This abrupt change in temperature, results in some varieties, particularly green varieties without any betaxanthin or betacyanin pigments, to experience serious damage to fruit quality. In this case, the edible portion of the fruits changes from an opaque solid appearance to a water soaked, translucent appearance. This phenomenon has been denoted "clearing" by growers. In contrast to the green fruited varieties, this purple 'DAR1-21-27 Purple' does not experience "clearing".

In the location where the varieties are grown in the cool coastal region of central California, normally the date of first picking is the middle of September and the date of last picking is April 30. Under optimal storage conditions of refrigeration and humidity control, this non climacteric fruit has a shelf life of about 3 weeks. The plant can withstand a few hours of 20 F with the only damage being to flowers and immature cladodes. Temperatures in the Salinas Valley where the plants are grown never exceed 98 F and the plants suffer no damage from these temperatures. The plant is has good vigor in producing new cladodes from March/April until late November.

The major disease is known as engrosamiento de cladodios (pad swelling) in Mexico that causes stunting of fruits and pads. Our recent research indicates this is caused by an Umbravirus that is transmitted by cowpea aphids. To date all commercial fruit type varieties are susceptible to this virus. The plant is also susceptible to damage from wild cochineal (*Dactylopius* spp) insects.

The invention claimed is:

1. A new and distinct purple fruited *Opuntia ficus indica* plant named 'DAR 1-21-27 Purple' substantially as illustrated and described, characterized by an increased Brix and firmness over any purple fruited cactus pear variety.

* * * * *